(12) United States Patent
Rahim

(10) Patent No.: US 11,215,586 B2
(45) Date of Patent: Jan. 4, 2022

(54) ULTRASOUND GAS SENSOR SYSTEM USING MACHINE LEARNING

(71) Applicant: AROMATIX, INC., Santa Clara, CA (US)

(72) Inventor: Chowdhury F. Rahim, Santa Clara, CA (US)

(73) Assignee: AROMATIX, INC., Santa Clara, CA (US)

( * ) Notice: Subject to any disclaimer, the term of this patent is extended or adjusted under 35 U.S.C. 154(b) by 0 days.

(21) Appl. No.: 15/750,448

(22) PCT Filed: Jan. 29, 2018

(86) PCT No.: PCT/US2018/015734
§ 371 (c)(1),
(2) Date: Feb. 5, 2018

(87) PCT Pub. No.: WO2018/140874
PCT Pub. Date: Aug. 2, 2018

(65) Prior Publication Data
US 2019/0391115 A1    Dec. 26, 2019

Related U.S. Application Data

(60) Provisional application No. 62/452,291, filed on Jan. 30, 2017.

(51) Int. Cl.
*G01N 29/44* (2006.01)
*G01N 29/036* (2006.01)
(Continued)

(52) U.S. Cl.
CPC ......... *G01N 29/036* (2013.01); *A61B 5/0836* (2013.01); *A61B 5/4821* (2013.01);
(Continued)

(58) Field of Classification Search
CPC .................. G01N 29/036; G01N 29/4481
(Continued)

(56) References Cited

U.S. PATENT DOCUMENTS 3,879,992 A    4/1975   Bartera
4,549,427 A    10/1985  Kolesar
(Continued)

FOREIGN PATENT DOCUMENTS

CN    106215299 A    12/2016
JP       60117131 A     6/1985
(Continued)

*Primary Examiner* — John Fitzgerald
*Assistant Examiner* — Rodney T Frank
(74) *Attorney, Agent, or Firm* — Tyler M. Jeffs; Fabian VanCott

(57) ABSTRACT

A system for measuring a gas concentration, the system including: a first oscillator including a first surface for placement in a sampling location, wherein the first oscillator oscillates at a frequency greater than 20,000 Hz but less than 300,000,000 Hz; a first counter to accumulate a count of oscillations of the first oscillator; and a comparator to calculate a difference between the accumulated counts of the first oscillator and a reference, wherein the difference calculated by the comparator is sampled at a frequency of less than 100 Hz.

18 Claims, 7 Drawing Sheets

(51) Int. Cl.
   *A61B 5/083* (2006.01)
   *A61B 5/00* (2006.01)
(52) U.S. Cl.
   CPC ....... *A61B 5/7267* (2013.01); *G01N 29/4481* (2013.01); *A61B 2560/0252* (2013.01); *G01N 2291/014* (2013.01); *G01N 2291/0215* (2013.01); *G01N 2291/02809* (2013.01); *G01N 2291/02845* (2013.01); *G01N 2291/02881* (2013.01)
(58) Field of Classification Search
   USPC .......................................................... 73/23.3
   See application file for complete search history.

(56) References Cited

U.S. PATENT DOCUMENTS

| | | |
|---|---|---|
| 4,637,987 A | 1/1987 | Minten et al. |
| 5,179,028 A | 1/1993 | Vali et al. |
| 5,339,675 A | 8/1994 | Dileo et al. |
| 5,445,008 A | 8/1995 | Wachter et al. |
| 5,719,324 A | 2/1998 | Thundat et al. |
| 6,041,642 A | 3/2000 | Duncan |
| 6,111,342 A | 8/2000 | Muramatsu et al. |
| 6,140,689 A | 10/2000 | Scheiter |
| 6,156,578 A | 12/2000 | Tom |
| 6,171,867 B1 | 1/2001 | Feucht |
| 6,257,048 B1 | 7/2001 | Hietala et al. |
| 6,598,459 B1 | 7/2003 | Fu |
| 7,303,530 B2 | 12/2007 | Barnes |
| 7,408,364 B1* | 8/2008 | Campbell ............ G01N 33/246 324/644 |
| 7,552,619 B2 | 6/2009 | Andle |
| 7,628,907 B2 | 12/2009 | Gu |
| 7,939,273 B2 | 5/2011 | Craighead et al. |
| 8,826,724 B2 | 9/2014 | Serban |
| 9,222,867 B2 | 12/2015 | Norling et al. |
| 9,354,202 B2 | 5/2016 | Medin et al. |
| 10,379,093 B2* | 8/2019 | Murphy ................ G01N 29/022 |
| 2003/0177813 A1 | 9/2003 | Sakamoto |
| 2008/0065290 A1* | 3/2008 | Breed ..................... G01L 17/00 701/31.4 |
| 2008/0196478 A1 | 8/2008 | Raghurama |
| 2010/0024533 A1 | 2/2010 | Kimura |
| 2015/0168958 A1* | 6/2015 | Downie ............... G05D 11/139 700/282 |
| 2016/0305920 A1 | 10/2016 | Murphy |
| 2017/0248513 A1 | 8/2017 | Liu |

FOREIGN PATENT DOCUMENTS

| | | |
|---|---|---|
| JP | 03223669 A | 10/1991 |
| JP | H-05232006 A | 9/1993 |
| SU | 1114941 A1 | 9/1984 |
| WO | WO-2014123519 A1 | 2/2013 |
| WO | WO-2017025840 A1 | 2/2017 |

* cited by examiner

ULTRASOUND GAS SENSOR SYSTEM USING MACHINE LEARNING

BACKGROUND

Chronic obstructive pulmonary disease ("COPD"), asthma, hypoventilation, and apnea patients have difficulty breathing. In these patients, the airways in the lungs are damaged and lead to shortness of breath, impacting everyday activities. The breathing in apnea patients may be suspended and this can be a result of many factors such as: drugs, trauma, sleep, age, and neurological disease.

Capnography is a monitoring device that measures the concentration of carbon dioxide in exhaled air and displays a numerical readout and waveform tracing. Capnography can detect and/or monitor apnea, hypoventilation, and COPD. Capnography may be used in the operation room and/or the emergency room. Capnography is a direct measure of the effectiveness of the lung in a patient. Current commercial tools for capnography utilize nondispersive infrared ("NDIR") technology.

BRIEF DESCRIPTION OF THE DRAWINGS

The accompanying drawings illustrate various examples of the principles described herein and are a part of the specification. The illustrated examples do not limit the scope of the claims.

Figure 1:
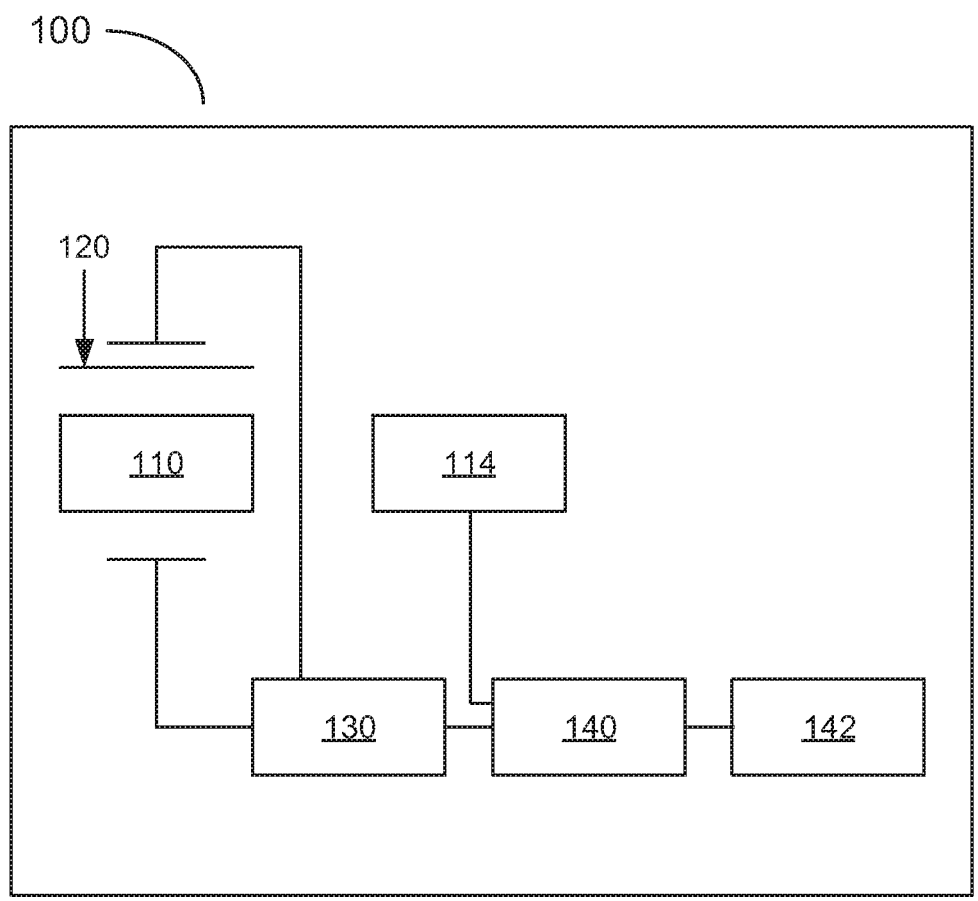
FIG. 1 shows a system for measuring a gas concentration according to an example consistent with the present specification.

Throughout the drawings, identical reference numbers designate similar, but not necessarily identical, elements. The figures are not necessarily to scale, and the size of some parts may be exaggerated or minimized to more clearly illustrate the example shown. The drawings provide examples and/or implementations consistent with the description. However, the description is not limited to the examples and/or implementations shown in the drawings.

DETAILED DESCRIPTION

One current commercial tool for capnography is nondispersive infrared ("NDIR") technology. However, NDIR has some disadvantages, including: high power dissipation, malfunctioning in the presence of moisture, poor sensitivity, non-disposable, difficult to operate, high cost, daily maintenance, and size. The power usage in NDIR makes NDIR a poor choice for use in a portable handheld device. However, the ongoing emphasis on home healthcare (HHC) and distributed diagnostics (DD) to reduce the cost of providing health care indicate a need for a home based solution. However, the described benefits are also useful in hospitals, doctor's offices, emergency services, and clinics.

The following approaches and devices may be used for a wide variety of purposes, including: capnography, dry mouth disease (halitosis), alcohol detection in human breath, anesthesia monitoring, food freshness detection, industrial gas sensors, etc. The devices and methods described may be used when the signal frequency to detect is changing at least at an order of magnitude lower than the sensor frequency dictated by the sensitivity for the system. This movement from the detection frequency to the monitoring frequency provides a basis to reduce the energy consumption of the system. Reduced energy consumption may reduce costs, increase session life of devices, facilitate portability, etc.

In an example, the system first uses digital counters by which the sensor signals are numerically measured for a precise time period and the value of the reference sensor counter is subtracted from the functionalized sensor counter. The resulting frequency can be anywhere between tens of KHz to low MHz.

Another power dissipation component is the power to wirelessly communicate the result of the digital section and/or the ML algorithm to another digital medium, such as the smartphone or a PC or a server or any other variant of such system. The frequency of the signal being monitored in Capnography, i.e. exhaled human breath, changes at milliseconds ("mS") to at most hundreds of mS. As such, the Shannon's sampling theorem can be applied and broadcast the signal at the lowest sampling rate for optimum power management without compromising the digitized signal frequency.

As such, an object of the present invention is to integrate the ultrasound gas sensor based oscillator for detecting carbon dioxide concentration with artificial intelligence tools to extract the gas concentration in the presence of the non-linear effects of humidity, temperature and bias voltage.

While the oscillating sensors operate at tens of MHz to hundreds of MHz to obtain the desired sensitivity, the signal that is being monitored may be relatively slow. Accordingly, the sensor signals can be down-converted to a substantially lower frequency, using less energy, without losing any relevant information of the underlying signal. Shannon's sampling theorem can be applied and the signal broadcast at the sampling rate selected for power management without compromising the digitized signal frequency. This can reduce the current draw to less than a milliamp when fully powered up. Additionally, sections of the system, such as: the analog logics, digital processor, and/or the machine learning (ML) block and/or sub-sections, may be separately powered down when the section and/or sub-section is not being used. Additionally, if the processing is moved to another device with its own power source, e.g. a laptop, a tablet, a cellphone, etc. then the life of the onboard power source can be further extended. Such devices may also provide storage and/or communication options. For example, the results may be encoded and/or encrypted and stored in a repository. Any and/or all of these techniques may be employed to reduce the power dissipation to the nanoWatts (nW) to low microWatts ($\mu$W) range.

Among other examples, this specification describes a system for measuring gas concentration, the system including: a first oscillator (110) including a first surface (120) for placement in a sampling location, wherein the first oscillator (110) oscillates at a frequency greater than 20,000 Hz but less than 300,000,000 Hz; a first counter (130) to accumulate a count of oscillations of the first oscillator (110); and a comparator (140) to calculate a difference between the accumulated counts of the first oscillator (110) and a reference (114), wherein the difference calculated by the comparator is sampled at a frequency of less than 100 Hz.

Among other examples, this specification also describes a system for measuring a gas concentration, the system including: a first oscillator including a first surface for placement in a sampling location, wherein the first oscillator oscillates at a frequency greater than 20,000 Hz but less than 300,000,000 Hz; and a first counter to accumulate a count of oscillations of the first oscillator, wherein a value of the first counter is sampled at a frequency of less than 100 Hz.

This specification also describes a system for gas measurement such as capnography, the system including: a first oscillator comprising a first surface for placement in a sampling location, wherein the first oscillator oscillates at a frequency greater than 20,000 Hz but less than 300,000,000 Hz; a second oscillator comprising a second surface for placement in the sampling location, wherein the second oscillator oscillates at a frequency greater than 20,000 Hz but less than 300,000,000 Hz and the first and second surfaces having different absorptions for a gas whose concentration is being determined by the system; a processor with an associated memory, the associated memory containing a training set produced by the first absorption surface and the second absorption surfaces when the first and second absorption surfaces are exposed to multiple gas compositions; and a machine learning system using the processor, counts of the first and second oscillators, and the training set to output a signal of gas composition at the sample location, wherein the counts of the first and second oscillators are preprocessed to identify vibration and filter vibration when present prior to being provided to the machine learning system.

Turning now to the figures, FIG. 1 shows a system (100) for measuring a gas concentration according to an example consistent with the present specification. The system (100) includes: a first oscillator (110) including a first surface (120) for placement in a sampling location, wherein the first oscillator (110) oscillates at a frequency greater than 20,000 Hz but less than 300,000,000 Hz; a first counter (130) to accumulate a count of oscillations of the first oscillator (110); and a comparator (140) to calculate a difference (142) between the accumulated counts of the first oscillator (110) and a reference (114), wherein the difference (142) calculated by the comparator is sampled at a frequency of less than 100 Hz.

The system (100) is a system (100) for measuring a gas at a sample location. The system (100) may include a removable probe that may be attached to a handheld device. The system may include a set of probes that may be attached to a handheld device, the different probes in the set of probes designed for different environments and/or for measuring different gases. The system (100) may be a fixed installation, for example mounted to a wall and/or conduit to monitor conditions. The system (110) may be integrated with other devices, including devices to provide medical therapy to a patient, devices to provide a neutralization agent into a gas stream, devices to absorb a gas, devices to provide a gas, etc.

The first oscillator (110) oscillates at a high (MHz) frequency at the sample location. Changes in mass to the first oscillator (110) impact the frequency of oscillation. For example, the addition of mass to the first oscillator (110) may increase the period and decrease the frequency. Decreases in mass of the surface of the oscillator, for example from desorption of gas from the surface, may decrease the period and increase the frequency of oscillation. The first oscillator (110) has a first surface (120) which oscillates. That is to say, the first surface (120) is not the fixed part of the first oscillator (110) but rather is associated with the moving side. The first surface (120) supports reversible adsorption of a gas.

The system (100) may use a quartz crystal microbalance ("QCM") sensors for the first oscillator (110). The first oscillator (110) may be a Capacitive Micromachined Ultrasound Transceivers ("CMUTs"), a Piezoelectric Micromachined Ultrasound Transceivers ("PMUTs") and/or a Microelectromechanical System ("MEMS"). The system (100) may be implemented as a Tow Tomas oscillator, a Sullen and Key configuration, a Colpitts oscillator, Clapp oscillator and/or other variations. The oscillators in these devices operating at high frequencies and accordingly draw power in several milliamps ("mA") to tens of mA. The high frequency used is a component of high power dissipation associated with these types of oscillators as sensors.

The first surface (120) may be modified to increase the adsorption of a gas. For example, the first surface (120) may be oxidized, coated, textured, and/or otherwise modified. In an example, the first surface (120) is a material deposited on a surface of the material used to form the first oscillator (110). For example, the first surface may be a metalized layer on a piezoelectric substrate. The first surface (120) may also function as an electrode for the first oscillator (110). The first surface (120) may be deposited on and/or formed from a metalizing layer on a surface of the first oscillator (110). The first surface (120) may be a coating. In an example, the first surface (120) is a functionalized coating selected to interact with carbon dioxide.

One approach to managing crystal and/or other oscillators is to extract measurements and perform a regression to identify the frequency of the oscillator. For example, voltage/time information could be processed using a Fast Fourier Transform (FFT). Other similar matrix-based techniques may be used. These approaches provide the ability to make determinations about frequency and identify noise sources and contributions. This additional information may be useful in other application, such as ultrasonic imaging. However, these approaches are also processor and power intensive. Performing such calculations in real-time for a system places additional requirements on the supporting processor(s)/logics. This additional processing capacity increases costs and power consumption.

Another approach is to use a first counter (130) to accumulate cycles of the first oscillator (110). If the variable being evaluated is the frequency shift of the first oscillator (110), then performing all the additional computation to regress the frequency using a transform and/or similar computational intensive method is surplus and wasteful. Instead, a first counter (130) accumulates cycles of the first oscillator (130). The first counter (130) may include a reset line. The first counter may trigger using condition selected from a range of different conditions, including passing a zero value, peak, valley, high-low transition, low-high transition, etc. While the logics of the first counter (130) need to operate at the expected frequency of the first oscillator (110), e.g., 10,000 Hz but less than 300,000,000 Hz, the rest of the system (100) may be operated at a lower frequency. In an example, the frequency of the first oscillator (110) is between 20 MHz and 100 MHz. The frequency of the first oscillator (110) may be between 60 MHz and 90 MHz. Operating at lower frequency reduces the power consumption. A common rule of thumb is that power consumption varies proportionally to the frequency and as the square of the voltage of the system (100).

Further, the gas concentration being monitored is a slow moving signal. Accordingly, sampling the signal on a sub 100 Hz basis does not make the information less timely. Accordingly, performing sampling and calculation at the lower frequency reduces power consumption without reducing the sensitivity to the behavior of the monitored system.

The comparator (140) compares the first counter (130) with a reference (114). The comparator (140) may be a logic that performs the comparison continuously. The comparator (140) may perform the comparison in response to a signal. The comparator (140) may be internal to a processor and/or may be a processor.

The difference (142) may be provided in a variety of suitable formats. The difference (142) may be output in a digital form. The difference (142) may be provided as an analog output. The difference may be provided internally and/or externally to the system (100).

The reference (114) provides something to assess changes in frequency of the first oscillator (110). In an example, the reference (114) is provided by a second oscillator placed at the sampling location. The second oscillator may be a crystal oscillator. The second oscillator includes a second surface. The second oscillator may oscillate at a frequency greater than 10,000 Hz but less than 300,000,000 Hz. The second oscillator may have an associated second counter to accumulate counts to form the reference. The use of two oscillators with two similar but not identical and different by not very different surfaces provides a control to detect changes to the frequency of the first oscillator (110) from other factors. These factors may be accounted for by comparing the count to the second oscillator. These factors may be confirmed by the redundant measure of the second counter. Examples of factors include: temperature changes, humidity changes, aging of the first oscillator (110), power supply irregularities to the first oscillator (110), etc. In an example, the difference in counts between the first oscillator (110) and the second oscillator is kept below 10%, 5%, 2%, 1%, and/or 0.3% of the oscillations of the first oscillator (110).

The second oscillator and second counter may be joined by an array of oscillators and/or sensors, where each oscillator includes a surface. The different surfaces may have different chemical composition, different surface area, different structure, different roughness, etc. to provide different responses to the target gas as well as to other factors which may influence the frequency of the first oscillator (110). In an example, the number of factors considered in a model of the gas concentration are less than the number of sensors, allowing the use of signal averaging and/or other statistical methods to increase the quality of the result.

The references (114) may be a count from a clock. The reference (114) may be a stored count from the first oscillator (110) over a fixed timeframe. In a sense, the reference (114) is a calibration for the count from the first counter (130). The reference (114) allows the behavior of the first oscillator (110) to be described as a change in frequency rather than an absolute frequency. This may decrease the number of needed digits to describe the performance of the first oscillator (110). For example, if the first oscillator is operating at 50,000,000 Hz, the at least eight decimal digits will be used to described the frequency in Hz. In contrast, if the offset between the first counter (130) and the reference (114) is 3,000 Hz then the change can be described in 4 decimal digits. The number of digits of the count of the first counter (130) may also be reduced by using a higher sampling frequency of the count and/or difference, this would work against reducing power consumption by keeping the processing frequency lower and reducing the output signal frequency.

The system (100) may be a system to measure a concentration of a gas. For example, the system (100) may measure carbon dioxide for capnography. Detection and monitoring of carbon dioxide has a number of other uses such as monitoring combustion, air quality, etc. The system (100) may also be useful to monitor carbon monoxide. Carbon monoxide is an indicator of combustion completeness as well as a safety concern. The system (100) may be used to monitor humidity. Humidity is relevant in many chemical and industrial processes. The system (100) may be used to measure an anesthesia agent. In an example, the system (100) may be able to measure the concentrations of multiple different anesthesia agents simultaneously using an array of oscillators with differing surfaces. The system (100) may be used to measure methane and/or a similar hydrocarbon gas. The system (100) may be used to measure ethanol, for example, to estimate the blood alcohol content of an impaired driver using the ethanol in their breath. The system (100) may be used to measure radon. Radon is a hazard which increases lung cancer risk.

Another way to use the first counter (130) and the reference (114) is to have the counter capable of incrementing and decrementing. For example, the first oscillator (110) may increment the counter with each cycle and a second oscillator would decrement the counter with each cycle. This uses a more complex first counter (130) which is capable of incrementing and decrementing. In another example, the signal from the first oscillator (110) is provided to a holding register, if a subsequent signal comes in from the first oscillator, the first counter (130) is incremented. If a signal from the reference (114) comes in the value in the holding register is dumped. Thus, the first counter would accumulate sequential signals from the first oscillator (110) when there was not an intervening signal from the reference (114). This setup may work where the counter counts sequential signals from reference without an intervening signal from the first oscillator (130). How the first counter (130) and/or a holding register are arranged may depend on the expected shift of the first oscillator (130) compared to any expected shift of the reference.

The first counter (130) may include a reset line. The reset line may provide a reset signal to the first counter (130). The reset line may provide a reset signal to multiple counters simultaneously. For example, the reset line might reset the first counter (130) and the second counter. This keeps the accumulating counts in multiple counters associated with a common window.

The reset signal may be provided to the reset line in response to sending and/or copying the count in the first counter (130) and/or the difference from the comparator (140). The system (100) may have a low frequency clock, e.g., 10 Hz, 1 Hz, 100 Hz, or 1 kHz, which triggers the exporting of the counts and/or difference(s) and resets the counters.

The system (100) may be a handheld unit. The system (100) may contain an isolated power source. For example, the system (100) may be battery powered. In battery powered systems, the benefits of reduced power consumption include increased battery life and working time for the system (100) on a single charge. The system (100) may be capable of operating for a week, two weeks, four weeks, two months, and/or three months without recharging and/or battery replacement. This long operational life facilitates home use as the patient doesn't need to remember to charge the device and/or change the batteries.

The system (100) may include a temperature sensor for placement at the sampling location. The temperature sensor may be a thermocouple, an infrared sensor, a resistance sensor, and/or another suitable sensor type. In an example, the first oscillator (110) and the temperature sensor, humidity sensor, and/or other sensors are integrated into a probe tip. The probe tip may include an array of oscillators. The probe tip may include fingers, filaments, and/or similar mechanical features to induce turbulent flow near the sensors and/or disrupt laminar flow. In an example, the sensors may be integrated into a component where the shape of the component influences the fluid dynamics at the sensor location(s).

The system (100) may include a humidity sensor (hygrometer) for placement at the sampling location. The humidity sensor may be a capacitive sensor, an impedance sensor, a conductivity sensor, and/or other type of humidity sensor. The humidity sensor may be integrated with the temperature sensor. The humidity sensor may be an oscillator with a modified surface, for example a hydrophilic surface.

The system (100) may include a bias voltage sensor. The bias voltage sensor may measure the bias voltage on the first oscillator (110). The bias voltage sensor may measure the bias voltage on the second oscillator. The system (100) may include a bias voltage sensor for each oscillator. The system (100) may include a bias voltage sensor which can sample multiple oscillators in sequence.

The system (100) may include a sensor to monitor an input voltage. The input voltage may be subject to transients. When a transient is detected, the system (100) may filter and/or compensate for the transient in the data from the oscillator(s), counter(s), and/or comparator. In an example, the system (100) drops compromised results. In an example, the system (100) corrects the compromised results using non-compromised results. In an example, the second order variation of the results is preserved which the frequency magnitude is scaled to reflect the adjacent uncompromised regions. For example, the mean may be linearly interpolated between two uncompromised regions and corrected results shifted and/or scaled to the interpolated mean. Other techniques for noise mitigation and/or compensation may similarly be used.

Figure 2:
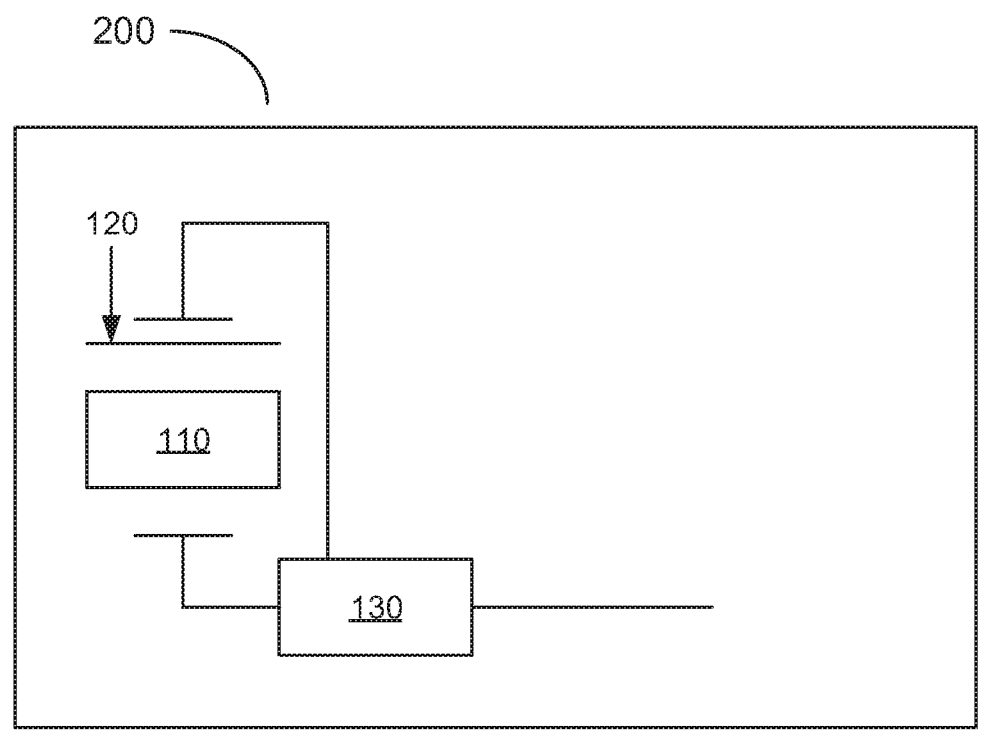
FIG. 2 shows a system for measuring a gas concentration according to an example consistent with the present specification.

FIG. 2 shows a system (200) for measuring a gas concentration according to an example consistent with the present specification. The system (200) includes: a first oscillator (110) comprising a first surface (120) for placement in a sampling location, wherein the first oscillator oscillates at a frequency greater than 20,000 Hz but less than 300,000,000 Hz; and a first counter (130) to accumulate a count of oscillations of the first oscillator (110), wherein a value of the first counter (130) is sampled at a frequency of less than 100 Hz. In an example, the first counter (130) is sampled at a frequency of no more than 1 kHz. The first counter (130) may be sampled at a frequency of no more than 10 Hz and/or 1 Hz.

This example can limit the high frequency activity to the first oscillator (110) and the first counter (130) while allowing the other elements of the system to operate at a lower frequency. By sampling the first counter (130) at a low rate, any high frequency information on the oscillation is not captured. However, for the gas signals being monitored, the relevant response may be of the order of 1 mS, 10 mS, 100 mS, and/or even 1 second or greater may be present. For example, monitoring fruit ripeness by ethylene compositions tolerates a relatively long response time compared with microseconds or even seconds. As a result, even frequencies such as 100 Hz, 10 Hz, or lower may be more frequent than is needed to provide all the relevant information in a timely manner. Some signals being measured with the system (200) may have response times on the order of seconds and/or minutes. Accordingly, sampling the signals at kHz and/or MHz frequencies does not increase the quality of measurement while consuming greater energy and processing resources. In contrast, reducing the sampling frequency and the data output frequency while limiting high speed operations to driving the first oscillator (130) uses the high frequency behavior where needed while avoiding the increased power consumption which would result from the output being assessed at high frequency. This approach of reducing the frequency of the data prior to evaluation works well with slow moving system where high frequency (e.g., MHz) measurement adds little value and a large amount of data to process.

The system (200) may further include: a second oscillator comprising a second surface for placement in the sampling location, wherein the second oscillator oscillates at a frequency greater than 20,000 Hz but less than 300,000,000 Hz; a second counter to accumulate a count of oscillations of the second oscillator, wherein a value of the second counter is sampled at a frequency equal to that of the first oscillator; and a comparator to compare accumulated counts of the first and second counters. As discussed above, using a second oscillator at the sampling location allows correction for changes in properties unrelated to the sampled gas concentration. The counts in the first and second counters may be accumulated over a shared sampling period. The length of the sampling period may be adjusted to accommodate other engineering factors, such as the sampling frequency of the output, the size of the counters, the frequency of the oscillator(s), etc. Further, having two oscillators at similar frequencies allows output and processing of the difference rather than the count values. Providing the data as a difference in counts is a significant attribute of low power transmission.

The first (120) and second surfaces have may have different absorptions of the gas to be measured, for example, carbon dioxide. The first (120) and second surfaces may similarly be selected to differentiate other gases. In an example, the first surface (120) has a strong adsorption of a target gas and the second surface has a low adsorption of the target gas. Further, the first surface (120) and the second surface may have similar responses to factors besides the target gas, for example, humidity, temperature, other gases.

Figure 3:
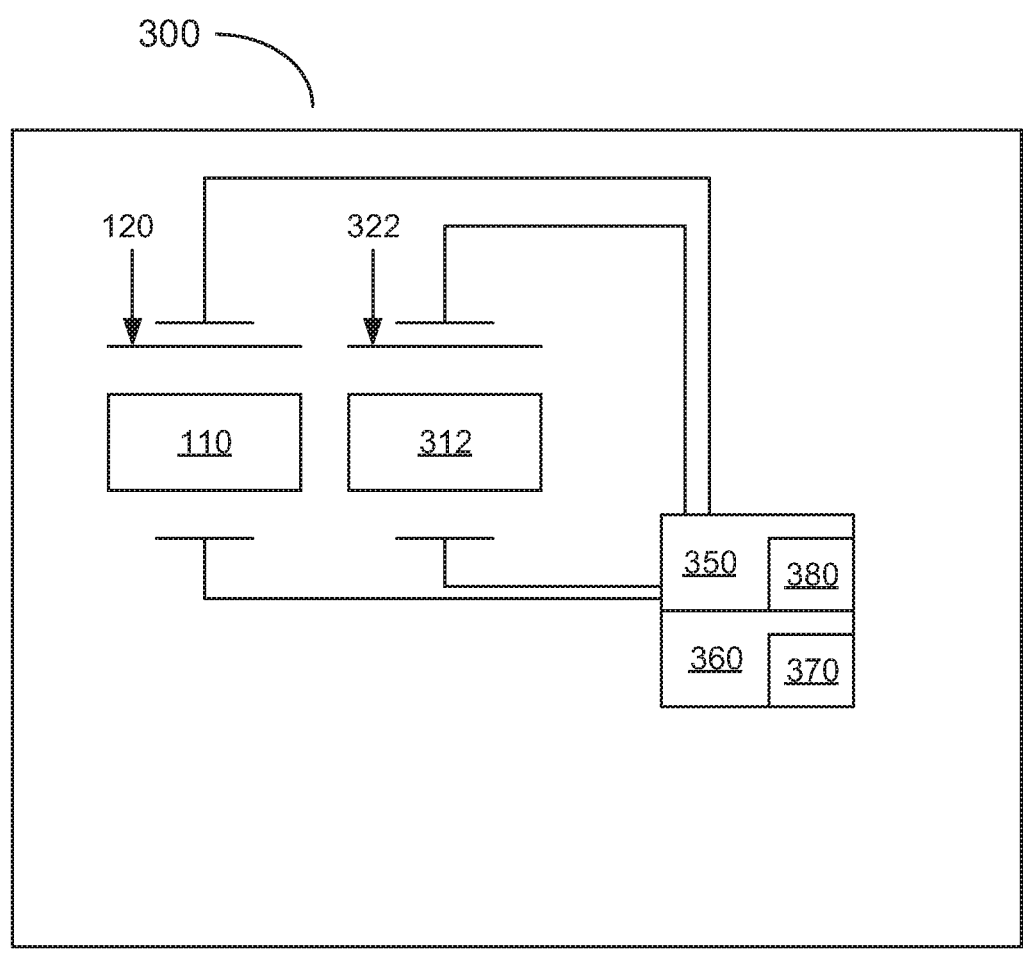
FIG. 3 shows a system for measuring a gas concentration according to an example consistent with the present specification

FIG. 3 shows a system (300) for detecting a specific gas, such as carbon dioxide, the system (300) including: a first oscillator (110) including a first surface (120) for placement in a sampling location, wherein the first oscillator (110) oscillates at a frequency greater than 20,000 Hz but less than 300,000,000 Hz; a second oscillator (312) including a second surface (322) for placement in the sampling location, wherein the second oscillator (312) oscillates at a frequency greater than 20,000 Hz but less than 300,000,000 Hz and the first (120) and second surfaces (322) having different absorptions for a gas whose concentration is being determined by the system (300); a processor (350) with an associated memory (360), the associated memory (360) containing a training set (370) produced by the first absorption surface (120) and the second absorption surface (322) when the first (120) and second absorption surfaces (322) are exposed to multiple gas compositions; and a machine learning system (380) using the processor (350), counts of the first oscillator (110) and the second oscillator (312), and the training set (370) to output a signal of gas composition at the sample location, wherein the counts of the first and second oscillators are preprocessed to identify vibration and filter vibration when present prior to being provided to the machine learning system.

The system (300) includes a digital signal processing system which includes, among other things, a machine learning system (380) to assess the composition of the gas at the sample location. The machine learning system (380) makes use of a processor (350) and a training set (370). The training set (370) facilitates calibration of the machine learning system (380) by providing controlled gas compositions (or measurements provided by other sources to measure the gas composition) and associated signal information from the first oscillator (110) and the second oscillator (312).

Figure 5:
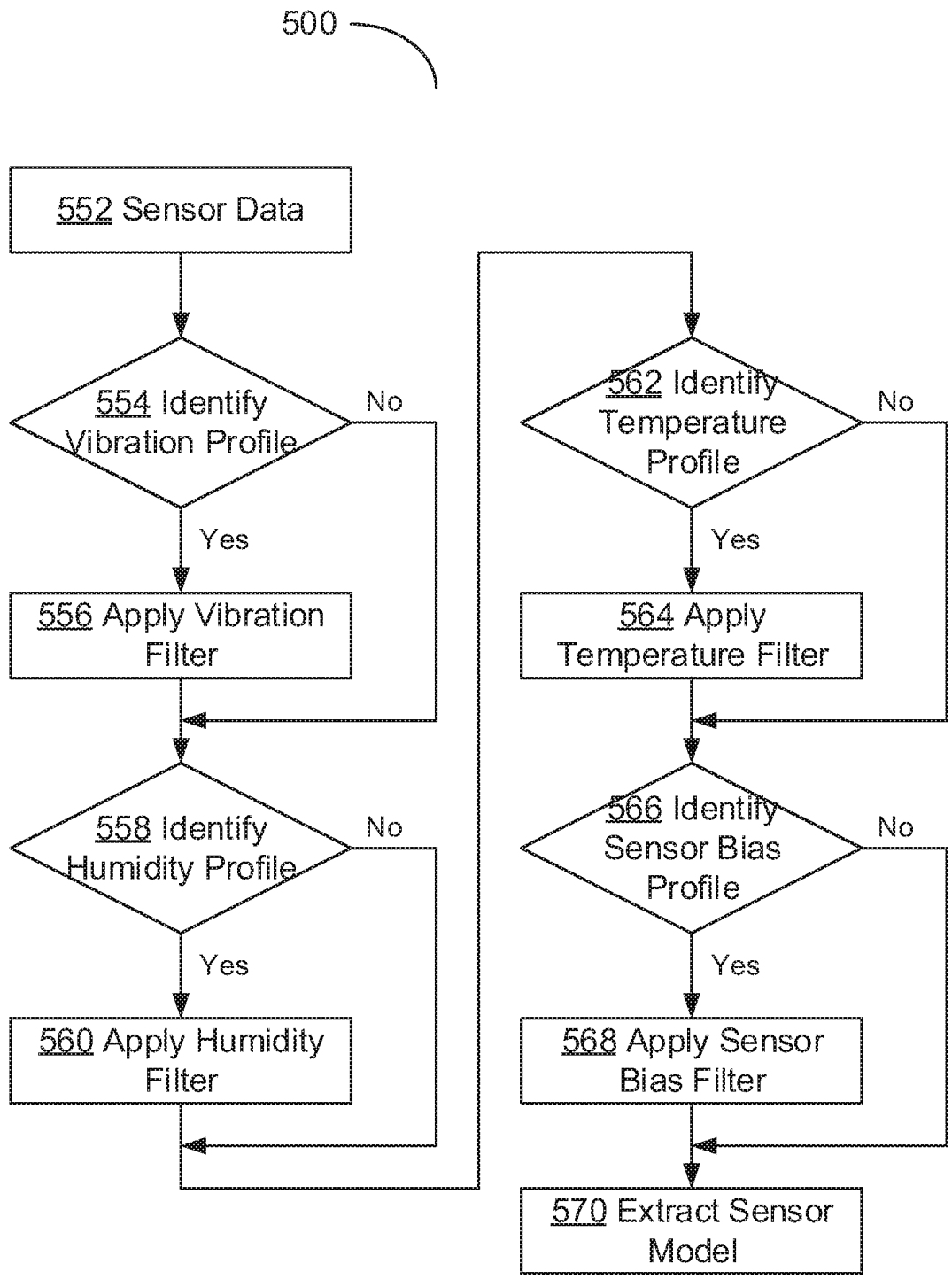
FIG. 5 shows a flowchart for preprocessing the sensor data according to an example consistent with the present specification.
Figure 6:
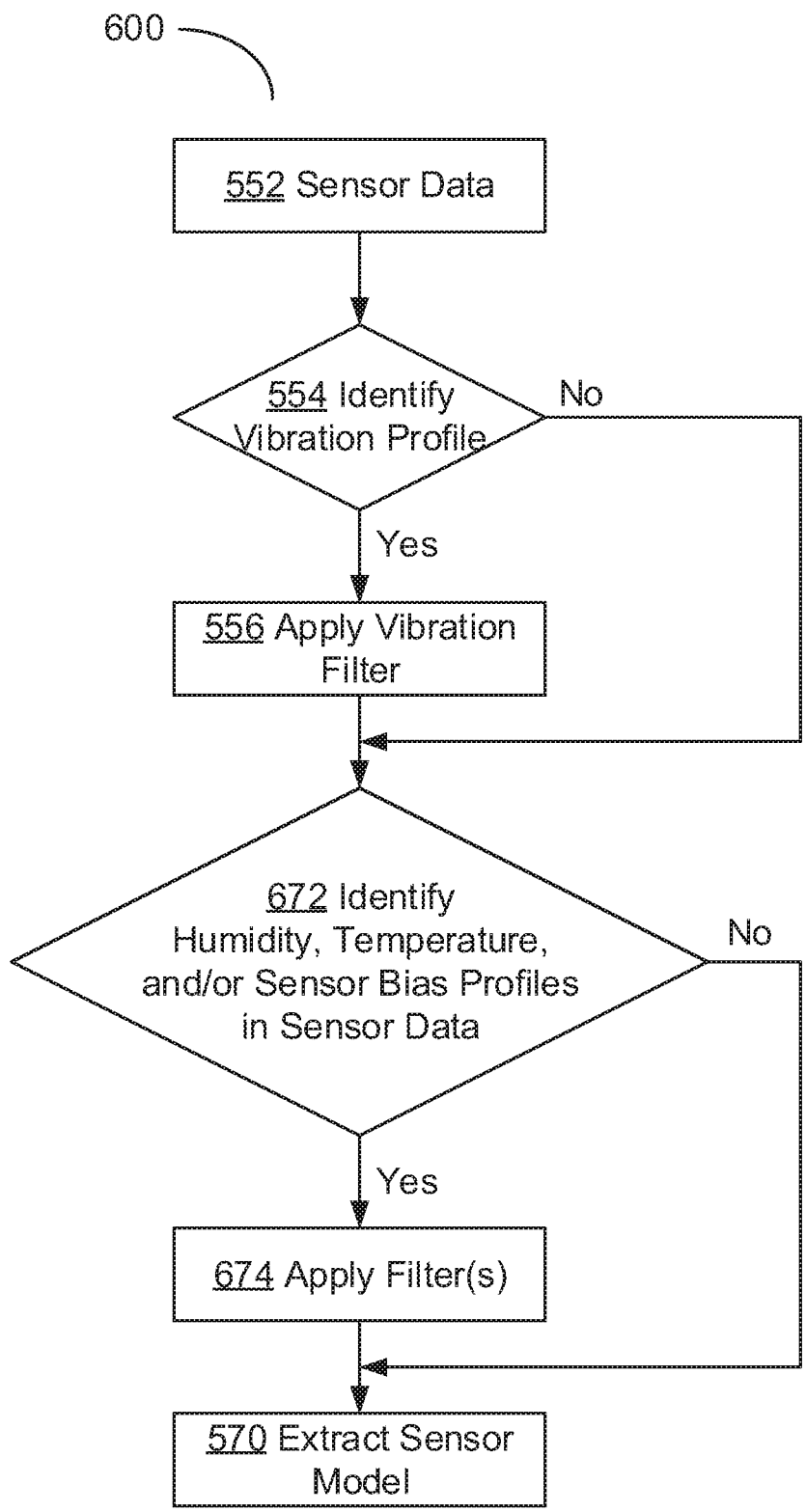
FIG. 6 shows a flowchart for preprocessing the sensor data according to an example consistent with the present specification.

The digital algorithm may perform preprocessing before the machine learning system (380) models the sensor. FIGS. 5 and 6 describe sequences to preprocess the output from the first (110) and the second oscillators (312) prior to providing information to a digital section of the system (300). The sampled digital result from the oscillators (110, 312) provides has some unique signatures which represent limitations of the ultrasound sensors. For example, one such signal is vibration. The digital algorithm may identify a vibration profile. If vibration is detected, the algorithm may add a digital filter. Using the digital filter may produce a cleaner input the machine learning system (380), increasing the effectiveness of the machine learning system (380). Similar preprocessing may successively identify and/or compensate for the profile of the humidity sensor, the temperature, sensor potential bias, power supply variations, and/or other variations.

Machine learning algorithm can be implemented in many variants, such as artificial neural network (ANN), support vector machine (SVM), K-nearest neighbor (KNN), and/or combinations of these. Similarly, other approaches may be applied, such as Bayesian Machine Learning and/or Kernel Based Machine Learning. However, traditional linear regression methods do not work well for ultrasound sensors. Accordingly, the use of other approaches, such as those described, allow better modeling of the sensors and results with greater accuracy. More information on machine learning systems is available, for example, in "Learning from data", Yaser Abu-Mostafa et al. (2012).

The effect of humidity, temperature, sensor bias, power supply variation and/or the gas composition may be extracted simultaneously using the above described techniques.

The second oscillator (312) is placed similarly to the first oscillator (310) at the sampling location. Placing multiple sensors in the sampling location allows for differentiation of the gas composition at the sampling location compared with other potentially confounding factors such as changes in temperature, humidity, and/or other gases.

The second oscillator (312) includes a second surface (322) which is located on the oscillating portion of the second oscillator (312) such that changes in mass of the second surface (322) produce changes in the frequency of oscillation of the second oscillator (312).

The processor (350) may be executed by a field programmable gate array ("FPGA") such as, Altera FPGA, a Cyclone V generation device. The processor (350) may perform the initial measurement of the two oscillators (110) (312). The processor (350) may receive information from other sensors, including humidity, temperature, and/or the bias voltage of the sensors. Data may be provided to a computer with a second processor, where further processing can be done in software. Examples of suitable software packages include MATLAB™ and/or GNU Octave™. The choice of the FPGA may depend on the partitioning of the operations between that done on the electronics and the rest done on the computer.

The processor (350) may be a computer processor where the processor has access to a memory (360) and the memory (360) contains a training set (370). The processor (350) may be associated with general purpose computer, such as a laptop, person computer, tablet, phone, etc. The processor may be associated with an application specific integrated circuit (ASIC) and/or similar implementation.

The memory (360) is a memory available to the processor (350). The memory (360) contains the training set (370). The training set (370) stored in the memory is used to train the machine learning system (380) to interpret data associated with the first oscillator (110) and second oscillator (312). In some examples, other oscillators and/or sensors are available to support the training set (370). Similarly, information about the output conditions of the training set runs may be available to aid calibration the machine learning system (380) to the actual conditions.

The training set (370) includes runs including identified compositions at controlled conditions. The runs from the training set (370) allow the machine learning system (380) to be calibrated to interpret the data from the sensors, including the oscillators (110) (312) in terms of the output variables, including composition of the target gas. The target gas may be carbon dioxide; however determinations of water vapor and/or other gases may help to produce reliable estimates of the carbon dioxide levels in the presence of varying humidity. The training set (370) includes sufficient parameters to develop the machine learning system (380) over the desired operating range. Factors such as the specific machine learning system (380), sensor bias, input transients, noise, sensor design, desired range, etc. may influence the number of runs in the training set (370).

Accordingly, the specific number of runs in the training set (370) may vary depending on the system (300) configuration and which gas and/or gases are being evaluated. The use of replicates, both true replicates and multiple sequential runs on a single setup can be useful to increase robustness of the response.

The training set (370) may include profiles of the first (110) and second oscillators (312) exposed to a matrix of test conditions, wherein the test conditions vary by humidity, target gas (e.g., carbon dioxide) concentration, and/or temperature. The training set (370) may include variation by bias voltage, input voltage, vibration, noise sources, etc. The training set (370) may include changes between a first gas composition and a second gas composition. For example, the system (300) may be set up to change from an ambient carbon dioxide mix to a higher carbon dioxide mix similar to exhaled air and back over a time frame similar to a respiratory cycle. The training set (370) may further include transition and/or change profiles where a competing gas, a contaminant, and/or a confounding element is introduced. The training set (370) may also include short pseudo steady state outputs at a variety of mixtures without tracking the changeover between different concentrations.

In an example, the runs forming the training set (370) are produced using additional sensors distinct from the system (300). The additional sensors may be used to provide verification of test conditions, aid in calibration, determine properties at the test location, etc. The system (300) may interface with a setup and/or calibration system to form the training set (370). The training set (370) may be stored in the memory (360). In another example, the training set (370) is stored in a storage medium and put into memory (360) as part of using the system (300). The training set (370) may be loaded into memory (360) used to train the machine learning system (380) and then removed from memory (360) once the machine learning system (380) is trained.

The machine learning system (380) may be a ANN, SVM, KNN, and/or any other variant mentioned earlier. In an example, a support vector machine algorithm is used. In an example, an artificial neural network is used.

Once a training parameters are developed, the results of the model may be stored in the system (300), for example in a memory (350). Once the system (300) receives a request to determine a gas concentration, the system (300) may use the stored measurements of the parameters, in conjunction with the oscillator frequency output from the output of the vibration sensor algorithm (FIG. 6), the parameters that are measured, such as humidity, temperature, sensor bias voltage, power supply voltage and the model. The system (300) may then determine a value of the gas concentration, a concentration range, and/or a threshold. Different types of outputs may use different regression and/or classification approaches among the machine learning (ML) algorithms.

The system (300) may include a humidity sensor for placement at the sampling location, wherein the machine learning system (380) uses an output from the humidity sensor when determining the gas composition. The system (300) may include a temperature sensor for placement at the sampling location, wherein the machine learning system (380) uses an output from the temperature sensor when determining the gas composition. The system (300) may include an array of oscillators, each oscillator comprising an associated surface, the associated surface having an adsorption for a gas, wherein cycle counts from the oscillators of the array of oscillators are provided as an input to the machine learning system (380) to determine a carbon dioxide and/or other gas concentration at the target location. The system (300) may include a bias voltage sensor. The system (300) may include an input voltage sensor.

Figure 4:
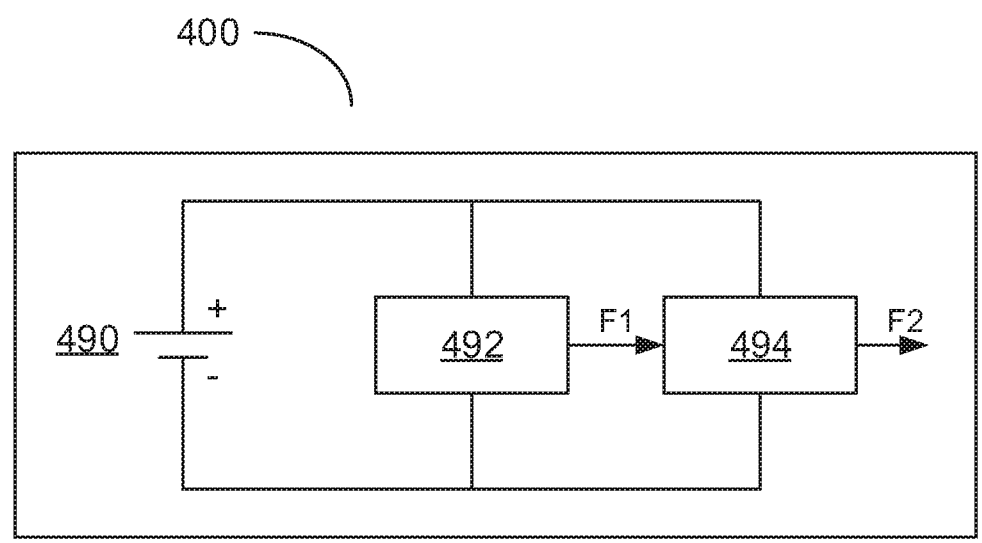
FIG. 4 shows an example of a system for gas measurement consistent with the present specification.

FIG. 4 shows an example of a system (400) for gas measurer lent consistent with the present specification. The system (400) includes an isolated power source (490), a sensor (492), and a logic (494). The sensor (492) provides an output at a first frequency F1, where F1 is from 10 to 300 MHz. The logic (494) provides an output at frequency F2, where F2 is typically no greater than 50,000 Hz.

The isolated power source (490) may be a battery. The isolated power (490) source may be a capacitor. The isolated power source (490) need not be connected to another power source during operation of the system (400). In an example, the system (400) is a handheld system and the isolated power source (490) is battery. The limiting high frequency activity to the sensor (492) and/or the logic (494) to monitor the output of the sensor (492) serves to limit power consumption by the system (400) and allowing the isolated power source (490) to provide increased lifetime without cords and/or inductive charging. In an example, the system (400) uses only the isolated power source for power. The system (400) may be rechargeable by connecting to an outlet or similar.

The sensor (492) may be a first oscillator (110) with a first surface (120) as described. The sensor (492) may be a combination of oscillators, surfaces, counters, and connecting logics. The sensor operates in the MHz region and provides an output in this frequency range. The information from the sensor (492) is converted by the logic (494) to a lower frequency for further use. For signals where the response is below 1 millisecond, the loss of the high frequency sampling produces equally useful monitoring without the power consumption and processing requirements associated with monitoring and/or processing MHz frequency signals.

The logic (494) may be analog and/or digital devices. The logic (494) may be implemented in hardware. The logic (494) may be an application specific integrated circuit (ASIC) and/or other integrated circuit. The logic may be implemented with a general purpose device that is configured to perform the conversion from high frequency to lower frequency output. In an example, the logic (494) is a counter to accumulate counts from the sensor (492).

FIG. 5 shows a flowchart of preprocessing the sensor data according to an example consistent with the present specification. The method (500) shown in FIG. 5 includes: receiving the sensor data (552), identifying a vibration profile (554) in the sensor data, selectively applying a vibration filter (556), identifying a humidity profile (558), selectively applying a humidity filter (560), identifying a temperature profile (562), selectively applying a temperature filter (564), identifying a sensor bias profile (566), selectively applying a sensor bias profile (568), and extracting a sensor model (570).

The method (500) may combine some of the operations shown. For example, the identification may be performed for all the correctable sources prior to applying the filter(s). Vibration signals are not being measured in this system, and can occur at any time. However the profiles of the signals in the frequency domain are observable and may be corrected with various statistical filters, such as averaging filter, the median filter, the mode filter, best of n-samples filters etc. Some of the other parameters, such as humidity, temperature, sensor bias, supply variation may be measured using sensors and corrected. The filters may be applied simultaneously and/or sequentially. Some profiles and filters may be removed. For example, in a system without a temperature sensor, it may not be reasonable to apply a temperature filter (564) regardless of whether a temperature profile is identified.

Receiving the sensor data (552) may include sending a request and/or accessing a register. The sensor output from the counters may undergo additional signal processing as shown in the FIGS. 5 and/or 6.

Identifying a vibration profile (554) in the sensor data is useful to identify whether to apply a vibration filter (556). Identifying a vibration profile (554) may also be used to determine parameters of the vibration filter applied and/or which vibration filter from a group of vibration filters to apply. The vibration profile may be observable as an abrupt shift in the frequency until the vibration disappears.

Selectively applying a vibration filter (556) includes applying a vibration profile based on the identification of a vibration profile in the sensor data. If there is no detectable vibration profile, then performing a vibration filter may degrade the data without a benefit in data quality. Accordingly, selectively applying the filters provides advantages over applying the filters to the data regardless of the characteristics of the sensor data. Once the vibration profile is identified, appropriate filtering may be performed to correct for the deviations introduced by the vibration. The remaining parameters may be measured with techniques in electronics and the processed data from the vibration filter is then systematically processed either serially (FIG. 5), i.e., one parameter at a time, and/or simultaneously (FIG. 6)

where all parameters, except the vibration data are input and the gas concentration is the resultant output.

Identifying a humidity profile (558) in the sensor data may include performing a time analysis of the sensor data. Identifying a humidity profile (558) may include assessing the output of a humidity sensor. In an example, the humidity sensor may be an oscillator similar to the first and/or second oscillator with a hydrophilic or hydrophobic surface compared to the first and/or second surfaces such that the surface of the humidity sensor has a different free energy of adsorption of water onto the surface of the humidity sensor. In an example, the humidity sensor may include a pair of oscillators with associated surfaces, one surface being hydrophilic and the other hydrophobic to maximize the difference in adsorption of water between the two surfaces. In an example, the humidity sensor is part of a larger array of sensors and humidity is assessed with a multifactorial analysis, for example, a principle component analysis (PCA) on the training set with the output aligned to with humidity and/or multiple factors. In an example, the PCA vector associated with humidity is trimmed of low weight inputs by the machine learning system and/or by a human reviewer prior to implementation as a detection method in the preprocessing.

Selectively applying a humidity filter (560) occurs if the humidity profile is detected in the sensor data. In an example, the humidity filter is adjusted based on factors identified in the humidity profile, such as, a voltage proportional to the humidity as recorded by a humidity sensor. The preprocessing may include multiple sequential filters being applied sequentially and/or serially based on the humidity profile detected. The preprocessing may include a number of different filters which are used depending on the result being determined. For example, a first filter may be used with carbon dioxide and a second filter may be used with carbon monoxide. A third filter may be used at a first temperature and a fourth filter may be used at a second temperature. The ability to develop specific filters for specific gas mixtures and/or other input conditions provides a method to increase the accuracy of the system without increasing resource use during operation. In an example, developing specific detection and filters may be performed as part of the training of the machine learning system (380) with the training set (370).

Identifying a temperature profile (562) may involve identifying a voltage proportional to the temperature as recorded by a temperature sensor and converting the voltage to a digital signal suitable for digital signal. Identifying a temperature profile (562) in the sensor data may be performed using method and techniques similar to those described above for identifying a humidity profile (558). Identifying the profiles may be performed sequentially and/or serially.

Selectively applying a temperature filter (564), if the temperature profile is detected in the sensor data. In an example, the temperature filter is adjusted based on factors identified in the temperature profile.

Identifying a sensor bias profile (566), by measuring a signal proportional to the sensor and converting the analog signal to a digital signal suitable for digital signal processing. The sensor bias profile may be determined by sampling the electrical connections to the sensor which drive the oscillation. In an example, the sensor is converted to a digital value. The digital value may be applied to a formulation to perform the correction. The digital value may be used with a lookup table to identify a filter and/or correction to apply to the sensor data.

Selectively applying a sensor bias correction (568) when a sensor bias profile is detected (556) helps to reduce the impact of sensor bias. In an example, the correction is a filter developed as part of the training set modeling of the sensor performance. The correction may be linear. The correction may be non-linear. The correction may be specific to a given humidity and/or temperature. The correction may be integrated into correction for humidity, temperature, and/or other factors being assessed to preprocess the sensor data.

Extracting a sensor model (570) may be performed using the machine learning system (380). The model provides parameters for the specific sensor and control combination tested in the training set. This provides a sensor specific model rather than a more generalized model for sensors of a given type. In an example, the sensor model is loaded with a generalized model for sensors of the type used and then modified using the training set to account for deviations by the actual sensor from the model profile.

The method (500) may also include monitoring the power supply voltage and correcting for and/or filtering the output based on the power supply voltage. The operations of detecting a potential factor and filtering/correcting based on that factor may be applied to other factors and noise sources. While temperature, humidity, bias voltage, and power supply voltage are explicitly recited here along with vibration detection, these corrections may be mixed and matched based on the engineering needs of the detector, the sensors, cost, robustness, and/or other design considerations.

FIG. 6 shows a flowchart of preprocessing the sensor data according to an example consistent with the present specification. The method (600) shown in FIG. 6 includes: receiving the sensor data (552); identifying a vibration profile in the sensor data (554); correcting for an identified vibration profile in the sensor data (556); identifying humidity, temperature, and/or sensor bias profiles in the sensor data (672); applying a filter or filters based on the detected profiles (674); and extracting a sensor model (570).

In the approach of FIG. 6 the vibration detection and filtering is performed and then adjustment for other factors is conducted concurrently. For example, a multifactorial filter that corrects for both humidity and temperature may be applied rather than applying a temperature filter and a separate humidity filter. This integrated approach may produce better corrections for non-linear effects and more complex interactions. This integrated approach may improve correction of related factors, such as humidity and temperature.

Figure 7:
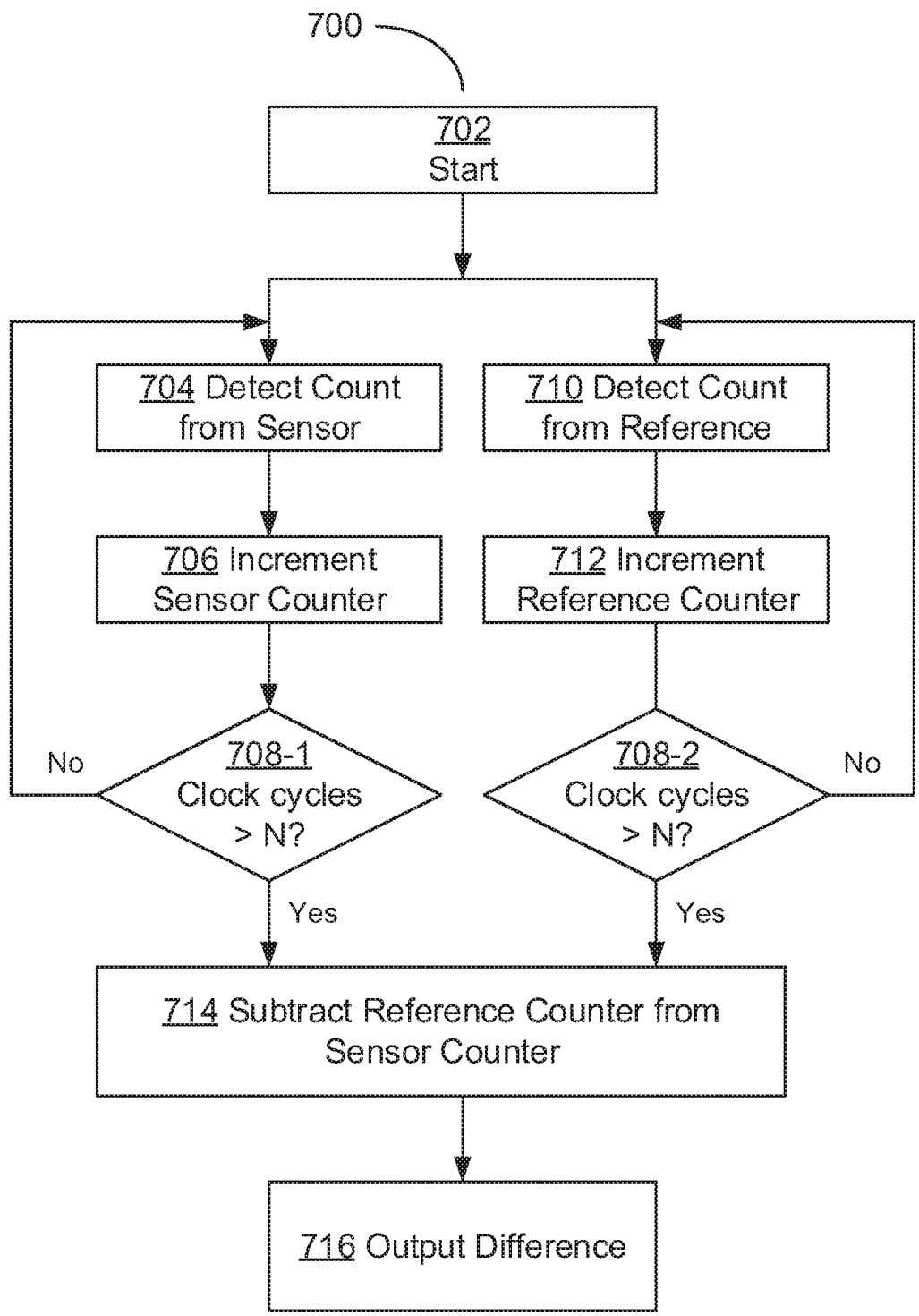
FIG. 7 shows an example of an implementation for the processing of the sensor and the reference counter according to an example consistent with the present specification.

FIG. 7 shows a flowchart for a method (700) according to one implementation consistent with the present specification. The method (700) includes start (702); detecting a count from the sensor (704); incrementing the sensor counter (706); detecting a count from the reference (710); incrementing the reference counter (712); repeat until N clock cycles have passed (708); subtracting the reference counter from the sensor counter (714); and outputting the difference (716).

The method (700) includes accumulating counts of the sensor and a reference over a period of N clock cycles. A difference in the accumulated counts is then determined. The summed time for N clock cycles forms the period for the output signal. In an example, this period is 1 mS, 10 mS, 100 mS, or 1000 mS. Similarly, other periods may be selected based on the other properties of the system and the specific gas signal being monitored. However, many gas signals do not contain information that is relevant in the sub 100 mS time frames, reducing the usefulness of operating at MHz frequencies. Further, operating the post processing at lower frequencies reduces the power consumption by the system. Coupled with the low overhead of using counts to describe the frequency information rather than attempting to regress the frequency from digital sampling, this approach can reduce the power consumption which in turn increases the session life of a portable device using an isolated power source.

The method (700) includes a start (702). The counters may continually reset until start (702), this assures the counters are empty prior to start (702). The counters may be reset as part of the start (702). The counters may be reset prior to receipt and/or issuance of a start signal. In an example, a start signal is provided by the clock cycle counter reaching N. In this approach, the counter resets every N cycles and the most recent difference may be stored on an output (716).

The method (700) involves detecting a count from the sensor (704). The detected signal may be a high/low transition, a low/high transition, a high signal, a low signal, and/or a similar signal.

Incrementing the sensor counter (706) may be performed directly by the detected signal. For example, the sensor counter may increment on high-low transitions and/or low-high transitions. This approach provides a straight forward implementation. Other designs may also be used, for example, where the detection of the count from the sensor is used to produce a signal to increment the sensor counter.

The sensor counter and the control counter continue to accumulate counts until a number of clock cycles (N) have passed (708). In FIG. 7, this activity is shown as 708-1 and 708-2 which are associated with the sensor counter and control counter loops respectively. Regulating the sampling time may be performed using a single clock counter/comparator. Regulating the sampling time may be performed using multiple components. The length of the window used to accumulate counts may be varied to accommodate design features such as register size, oscillator speed, etc. The use of the same length window for both the sensor counter and the control counter facilitates comparison of the data. Further, using the same window for both counters is readily implemented and keeps the control correlated with the sensor. The advantages of using a shared window should not be interpreted as preventing this application from covering non-shared window implementations. While non-shared window approaches are more complex, they may be useful in some circumstances depending on other design constraints.

In an example, the clock has a frequency similar to the frequency of the sensor. For example, the clock may have a frequency within 1%, 2%, 5%, and/or 10% of the sensor frequency. The use of a clock with a frequency multiple orders of magnitude lower than the sensor frequency may result in increased noise. However, averaging the results over multiple slower clock cycles may mitigate the noise as the increase in cycles in a measurement period comes from the adjacent measurement periods. The effectiveness of averaging may depend on the clock period, the response of the gas concentration signal being measured, and/or other periodic contributions in the system.

Detecting a count from the reference (710) depends on the reference. In an example, the reference is a device similar to the sensor but without the specificity to the target gas. The detection for the references and the sensor may be the same in this approach. This may allow the use of shared components for both the sensor and reference counters. The counters may be formed in a substrate using a shared set of processes. The ability to use components/counters formed in the same operations may reduce the offset between the control and the sensor, for example, for thresholds, latency, material effects, etc. Often the ability to form multiple similar devices on a substrate is only marginally more expensive than forming single device.

Incrementing the reference counter (712) may be similar to incrementing the sensor counter. In an example, the reference counter may be decremented so that determining the difference is an addition operation between a negative reference count and a positive sensor count.

Subtracting the reference counter from the sensor counter (714) may be performed in hardware and/or software. In an example, the count for the sensor and the count for the control are output to a processor which performs this operation. The subtraction may be performed by having one counter decrement and the other increment and then adding the results.

Outputting the difference (716) may be putting the difference in a storage register and/or transferring to memory. The difference may be retained in hardware for additional operations. The difference may be available on a port for sampling. Outputting the difference (716) may include providing a signal that the difference has been calculated and is available to a processor.

It will be appreciated that, within the principles described by this specification, a vast number of variations exist. It should also be appreciated that the examples described are only examples, and are not intended to limit the scope, applicability, or construction of the claims in any way.

What is claimed is:

1. A system for gas measurement, the system comprising:
a first oscillator comprising a first surface for placement in a sampling location, wherein the first oscillator oscillates at a frequency greater than 20,000 Hz but less than 300,000,000 Hz;
a second oscillator comprising a second surface for placement in the sampling location, wherein the second oscillator oscillates at a frequency greater than 20,000 Hz but less than 300,000,000 Hz and the first and second surfaces having different absorptions for a gas whose concentration is being determined by the system;
a processor with an associated memory, the associated memory containing a training set produced by the first absorption surface and the second absorption surfaces when the first and second absorption surfaces are oscillated when exposed to multiple measured gas compositions; and
a machine learning system using the processor, counts of oscillations of the first and second oscillators, and the training set to output a signal of gas composition at the sample location,
wherein an output of the first oscillator is processed at a frequency of no greater than 1000 Hz and an output of the second oscillator is processed at a frequency of no greater than 1000 Hz.

2. The system of claim 1, further comprising a humidity sensor for placement at the sampling location, wherein the machine learning system uses an output from the humidity sensor when determining the gas composition and wherein the humidity sensor comprises a third oscillator.

3. The system of claim 1, further comprising a temperature sensor for placement at the sampling location, wherein the machine learning system uses an output from the temperature sensor when determining the gas composition.

4. The system of claim 1, further comprising a digital signal processing circuit which performs preprocessing to remove effects of vibration on output of the oscillators.

5. The system of claim 1, wherein the training set comprises profiles of the first and second oscillators exposed to a matrix of test conditions, wherein the test conditions vary by humidity, gas concentration, and temperature.

6. The system of claim 1, further comprising:
a first counter to accumulate a count of oscillations of the first oscillator and a second counter to accumulate a count of oscillations of the second oscillator; and
a comparator to calculate a difference between accumulated counts of the first and second counters;
the machine learning system using output of the comparator to represent the counts of the first and second oscillators.

7. The system of claim 6, wherein the output of the comparator is sampled at a frequency of no greater than 100 Hz.

8. The system of claim 1, wherein the first oscillator is selected from a group consisting of a capacitive micromachined ultrasonic transducer (CMUT), a piezoelectric micromachined ultrasonic transducers (PMUT), and a quartz crystal microbalance (QCM).

9. The system of claim 1, wherein the first oscillator and second oscillator are located on a location selected from the group consisting of a probe tip and a module.

10. The system of claim 9, wherein a temperature sensor and a humidity sensor are located on the location.

11. The system of claim 1, wherein the first surface is a metalized, vibrating layer.

12. The system of claim 1, wherein the training set comprises a respiratory cycle.

13. The system of claim 1, wherein the frequency of the first oscillator varies by gas concentration.

14. The system of claim 1, wherein the counts of the first and second oscillators are preprocessed using a multifactorial filter to simultaneously compensate for multiple environmental conditions.

15. The system of claim 1, further comprising a removable probe attached to a handheld device, wherein the oscillators are located at a tip of the removable probe.

16. A system for gas concentration measurement, the system comprising:
a first oscillator comprising a first surface for placement in a sampling location, wherein the first oscillator oscillates at a frequency greater than 20,000 Hz but less than 300,000,000 Hz and a gas absorbed on the first surface slows oscillation of the first oscillator;
a second oscillator comprising a second surface for placement in the sampling location, wherein the second oscillator oscillates at a frequency greater than 20,000 Hz but less than 300,000,000 Hz and the first and second surfaces having different absorptions for a gas whose concentration is being determined by the system;
a first counter to accumulate a count of oscillations of the first oscillator and a second counter to accumulate a count of oscillations of the second oscillator;
a comparator to calculate a difference between accumulated counts of the first and second counters;
a processor with an associated memory, the associated memory containing a training set produced by the first absorption surface and the second absorption surfaces when the first and second absorption surfaces are oscillated when exposed to multiple controlled or measured gas compositions; and
a machine learning system using the processor, an output of the comparator, and the training set to output a signal of a gas concentration at the sample location, wherein an output of the comparator is sampled at a frequency of no greater than 1000 Hz.

17. A system for gas measurement, the system comprising:
a first oscillator comprising a first surface for placement in a sampling location, wherein an output of the first oscillator is processed at a frequency of no greater than 100 Hz;
a second oscillator comprising a second surface for placement in the sampling location, wherein the first and second surfaces having different absorptions for a gas whose concentration is being determined by the system, wherein output of the second oscillator is processed at a frequency of no greater than 100 Hz;
a processor with an associated memory, the associated memory containing a training set produced by the first absorption surface and the second absorption surfaces when the first and second absorption surfaces are exposed to multiple gas compositions; and
a machine learning system using the processor, counts of the first and second oscillators, and the training set to output a signal of gas composition at the sample location.

18. The system of claim 16, wherein the output of the comparator is sampled at less than 100 Hz.

* * * * *